(12) United States Patent
Brannan

(10) Patent No.: US 10,856,940 B2
(45) Date of Patent: Dec. 8, 2020

(54) ABLATION ANTENNA INCLUDING CUSTOMIZABLE REFLECTORS

(71) Applicant: COVIDIEN LP, Mansfield, MA (US)

(72) Inventor: Joseph D. Brannan, Lyons, CO (US)

(73) Assignee: Covidien LP, Mansfield, MA (US)

( * ) Notice: Subject to any disclaimer, the term of this patent is extended or adjusted under 35 U.S.C. 154(b) by 400 days.

(21) Appl. No.: 15/058,485

(22) Filed: Mar. 2, 2016

(65) Prior Publication Data

US 2017/0252106 A1    Sep. 7, 2017

(51) Int. Cl.
*A61B 18/18* (2006.01)
*A61B 18/00* (2006.01)

(52) U.S. Cl.
CPC ............ *A61B 18/1815* (2013.01); *A61B 2018/00148* (2013.01); *A61B 2018/00577* (2013.01); *A61B 2018/1892* (2013.01)

(58) Field of Classification Search
CPC ..... A61B 18/1815; A61B 18/18; A61B 18/00; A61B 2018/1892; A61B 2018/20553; A61B 2018/2255; A61B 2018/2261; A61B 2018/2266; A61B 2018/2272; A61B 2018/2283; A61B 2018/2285; A61B 2018/00577; A61B 18/20; A61B 2018/1807
See application file for complete search history.

(56) References Cited

U.S. PATENT DOCUMENTS

| | | |
|---|---|---|
| 6,142,994 A | 11/2000 | Swanson et al. |
| 6,471,696 B1 | 10/2002 | Berube et al. |
| 7,226,446 B1 | 6/2007 | Mody et al. |
| 7,306,588 B2 | 12/2007 | Loeb et al. |
| 7,311,702 B2 | 12/2007 | Tallarida et al. |
| 7,942,871 B2 | 5/2011 | Thapliyal et al. |
| 7,950,397 B2 | 5/2011 | Thapliyal et al. |
| 8,328,799 B2 | 12/2012 | Brannan |

(Continued)

FOREIGN PATENT DOCUMENTS

| | | |
|---|---|---|
| JP | 201178756 A | 4/2011 |
| JP | 2012-101080 A | 5/2012 |
| JP | 2012-217855 A | 11/2012 |

OTHER PUBLICATIONS

Japanese Notice of Allowance for Application No. 2017-036764 dated Apr. 5, 2018 with English translation, 6 pages.

(Continued)

*Primary Examiner* — Eun Hwa Kim
*Assistant Examiner* — Catherine Premraj
(74) *Attorney, Agent, or Firm* — Carter, DeLuca & Farrell LLP

(57) ABSTRACT

An ablation system for directing energy to a target volume of tissue is provided. The ablation system comprises an ablation antenna probe including at least one radiating portion configured to output electromagnetic radiation and at least one electromagnetic shielding reflector configured for removable positioning on the antenna probe. The at least one electromagnetic shielding reflector is configured to block electromagnetic radiation from the at least one radiating portion through the at least one electromagnetic shielding reflector such that a particular directionality of the electromagnetic radiation from the at least one radiation portion to a target volume of tissue is achieved.

15 Claims, 12 Drawing Sheets

(56) References Cited

U.S. PATENT DOCUMENTS

| | | |
|---|---|---|
| 8,328,800 B2 | 12/2012 | Brannan |
| 2001/0056279 A1 | 12/2001 | Odell et al. |
| 2002/0077550 A1 | 6/2002 | Rabiner et al. |
| 2003/0050630 A1 | 3/2003 | Mody et al. |
| 2003/0050631 A1 | 3/2003 | Mody et al. |
| 2003/0069575 A1 | 4/2003 | Chin et al. |
| 2003/0073988 A1 | 4/2003 | Berube et al. |
| 2003/0109862 A1* | 6/2003 | Prakash .............. A61B 18/12 606/33 |
| 2005/0015083 A1 | 1/2005 | Koblish et al. |
| 2007/0203480 A1 | 8/2007 | Mody et al. |
| 2008/0033422 A1* | 2/2008 | Turner .............. A61B 18/18 606/33 |
| 2011/0077633 A1* | 3/2011 | Bonn .............. A61B 18/1815 606/33 |
| 2011/0184391 A1* | 7/2011 | Aljuri .............. A61B 18/04 606/2 |
| 2012/0310228 A1* | 12/2012 | Bonn .............. A61B 18/1815 606/33 |
| 2014/0056028 A1* | 2/2014 | Nichol .............. G02B 6/0065 362/611 |
| 2014/0200403 A1 | 7/2014 | West et al. |
| 2015/0174390 A1 | 6/2015 | Nobis et al. |

OTHER PUBLICATIONS

Canadian Office Action for Application No. 2,959,010 dated Oct. 24, 2017 (4 pages).
Japanese Office Action for application No. 2017-036764 dated Dec. 27, 2017 with English translation (11 pages).
Extended European Search Report dated Jul. 27, 2017 in corresponding European Patent Application No. 17158881.7.
Canadian Office Action issued in corresponding Appl. No. CA 2,959,010 dated Nov. 16, 2018 (5 pages).
European Examination Report for application No. 17 158 881.7 dated Jun. 14, 2018 (3 pages).
Australian Examination Report dated Feb. 15, 2019 issed in corresponding AU Appln. No. 2018206780.
European Examination Report dated Mar. 28, 2019 issued in corresponding EP Appln. No. 17158881.7.
Chinese Office Action dated Oct. 12, 2019 issued in corresponding CN Appln. No. 201710118720.1.

* cited by examiner

ABLATION ANTENNA INCLUDING CUSTOMIZABLE REFLECTORS

BACKGROUND

1. Technical Field

The present disclosure relates to surgical devices for treating tissue. More particularly, the present disclosure relates to ablation antennas including customizable reflectors to facilitate the selective ablation of tissue.

2. Discussion of Related Art

Treatment of certain diseases requires the destruction of malignant tissue growths, e.g., tumors. Electromagnetic radiation can be used to heat and destroy tumor cells. Treatment may involve inserting ablation probes into or adjacent tissues where cancerous tumors have been identified. Once the probes are positioned, electromagnetic energy is passed through the probes into surrounding tissue to treat, e.g., heat, ablate and/or coagulate tissue. Microwave energy is sometimes utilized to perform these methods.

Typically, microwave apparatus for use in ablation procedures include a microwave generator that functions as an energy source, and a microwave surgical instrument (e.g., microwave ablation probe) having an antenna assembly for supplying the energy to the target tissue. There are several types of microwave antenna assemblies, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors, which are linearly aligned and positioned end-to-end relative to one another with an electrical insulator placed therebetween. Helical antenna assemblies include a helically-shaped conductor connected to a ground plane. Helical antenna assemblies can operate in a number of modes including normal mode (broadside), in which the field radiated by the helix is maximum in a perpendicular plane to the helix axis, and axial mode (end fire), in which maximum radiation is along the helix axis.

Some ablation targeted lesions are too small or too hard to be punctured by an ablation probe. In these cases, doctors may place the probe as close as possible to the lesion and perform an ablation. With non-directional ablation probes, the ablation may radiate to both sides of the probe, which may damage healthy tissue located on the non-tumor side of the radiating section. During certain procedures, it can be difficult to assess the extent to which the microwave energy will radiate into the surrounding tissue, making it difficult to determine the area or volume of surrounding tissue that will be ablated. Directional ablation probes have been developed that target specific areas of tissue. These devices work simply by orienting the antenna towards the target tissue and away from critical tissue structures that should not be damaged. Typically, directional ablation probes will only emit radiation from specified areas of the antenna, such as windows, slots, or junctions.

However, directional ablation probes are often more expensive than their non-directional counterparts. Exacerbating the cost, directional ablation probes are used infrequently due to the limited number of procedures that require them. Current directional ablation probes may be designed for a specific procedure, and may have limited versatility. Often, in a surgical procedure requiring tissue ablation, a surgeon may need precision targeting for only part of the procedure. Once the part of the procedure where precision targeting is required is completed, the surgeon must then switch between the directional ablation probe to a non-directional ablation probe when precision targeting is neither required nor sufficient for the remainder of the procedure. The surgeon then is required to retool, or use multiple ablation probes for the same patient, which can be cumbersome, inefficient, and time consuming. There exists a need for achieving cost-effective directional tissue ablation without having to retool or use cumbersome directional ablation probes.

SUMMARY

As can be appreciated, an ablation system for directing energy to a target volume of tissue may prove useful in the surgical arena.

An aspect of the present disclosure provides an ablation antenna probe including at least one radiating portion configured to output electromagnetic radiation. At least one electromagnetic shielding reflector may be configured for removable positioning on the antenna probe and may be configured to block electromagnetic radiation from the at least one radiating portion through the electromagnetic shielding reflector such that a particular directionality of the electromagnetic radiation from the radiating portion to a target volume of tissue is achieved.

The electromagnetic shielding reflector may include an electromagnetic shielding material wherein an adhesive adhered to a bottom surface of the electromagnetic shielding material. The electromagnetic shielding reflector may further include a release liner releasably attached to the adhesive. The adhesive may be pressure sensitive.

The electromagnetic shielding material may comprise is selected from the group consisting of silver, copper, gold, aluminum, brass, bronze, tin, lead, nickel, stainless steel, electrically conductive polymer, mumetal, and superpermalloy. The electromagnetic shielding material may also be a composite material. The electromagnetic shielding reflector has a configuration selected from the group consisting of a strip of material, a sheet, a foil, a mesh, a tape, and a coating.

According to another aspect of the present disclosure, the electromagnetic shielding reflector is configured as a tube and configured for fitted placement over at least a portion of the ablation antenna probe. The tube may be a heatshrink tube. Additionally, an adhesive may be disposed on the inner surface of the tube.

The tube may define at least one window configured to permit passage of electromagnetic radiation therethrough. Further, a removable screen may be configured to cover the at least one window to thereby inhibit electromagnetic radiation therethrough.

According to another aspect of the present disclosure, the electromagnetic shielding reflector may be a cap configured for positioning about a distal tip of the ablation antenna probe.

According to yet another aspect of the present disclosure, a kit for use with an ablation device may be provided, comprising a plurality of electromagnetic shielding reflectors. Each electromagnetic shielding reflector may be configured for placement on an ablation antenna probe, wherein each electromagnetic shielding reflector is configured to block electromagnetic radiation from at least one radiating portion of the antenna probe through each electromagnetic shielding reflector such that a particular directionality of the electromagnetic radiation from the at least one radiation portion to a target volume of tissue is achieved. At least two of the plurality of electromagnetic shielding reflectors may define different configurations so as to provide different directionality.

At least one of the electromagnetic shielding reflectors may include an electromagnetically shielding material, an adhesive adhered to a bottom surface of the electromagnetically shielding material, and a release liner releasably attached to the adhesive. In addition, at least one of the electromagnetic shielding reflectors includes a tube configured for fitted placement over at least a portion of the ablation antenna probe. The kit may further include a cap configured for placement over a distal tip of the ablation antenna probe.

According to yet another aspect of the present disclosure, a method of directing radiation to a target volume of tissue is provided. The method may comprise providing an ablation antenna probe including a radiating portion configured to output electromagnetic radiation, placing at least one electromagnetic shielding reflector on the ablation antenna probe to achieve a particular directionality of electromagnetic radiation emission, and activating the ablation antenna probe to emit electromagnetic radiation according to the particular directionality of electromagnetic radiation emission defined by the at least one electromagnetic shielding reflector.

BRIEF DESCRIPTION OF THE DRAWINGS

Objects and features of the present disclosure will become apparent to those of ordinary skill in the art when descriptions of various embodiments thereof are read with reference to the accompanying drawings, of which.

DETAILED DESCRIPTION

Figure 1:
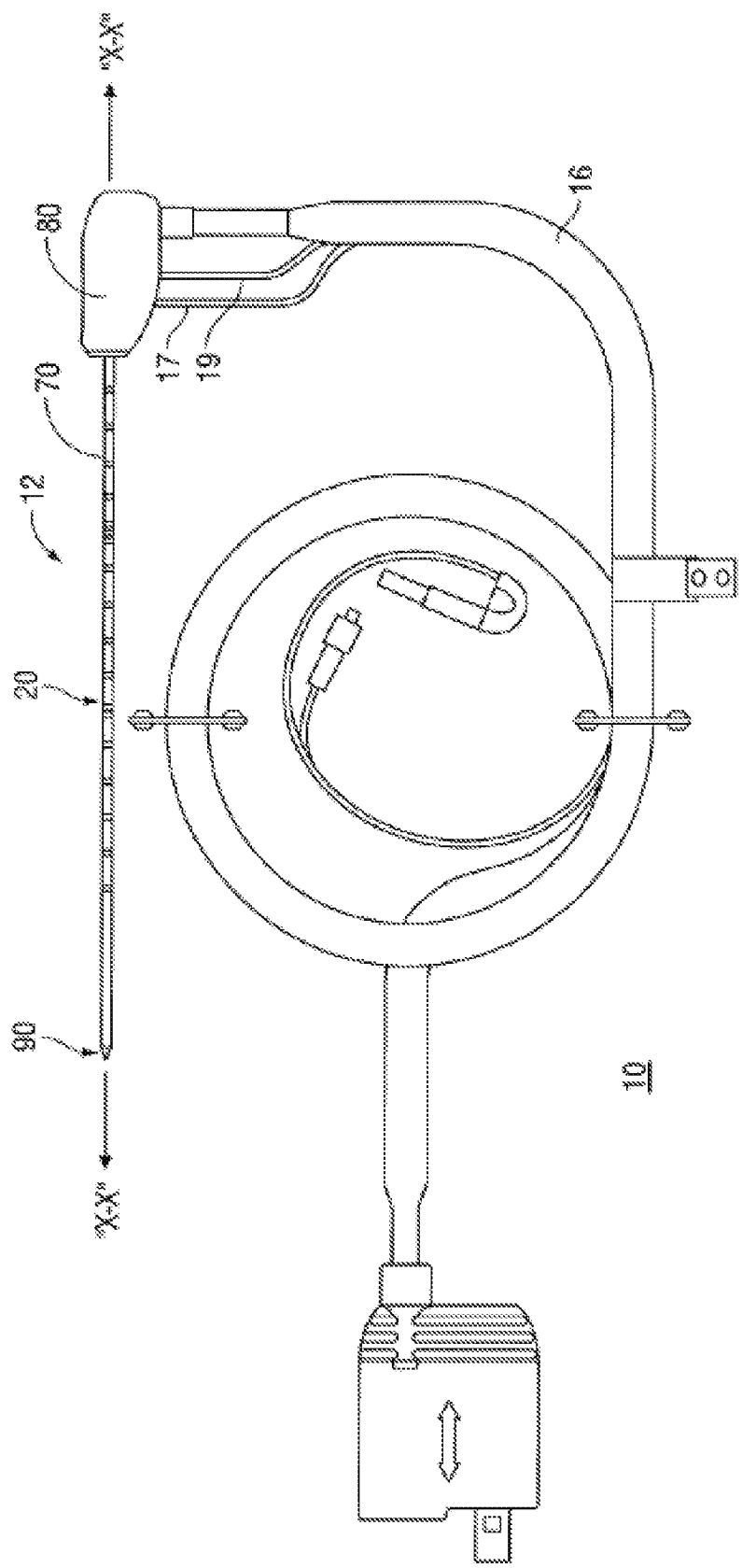
FIG. 1 is a side view of a microwave ablation system provided in accordance with the present disclosure.
Figure 2:
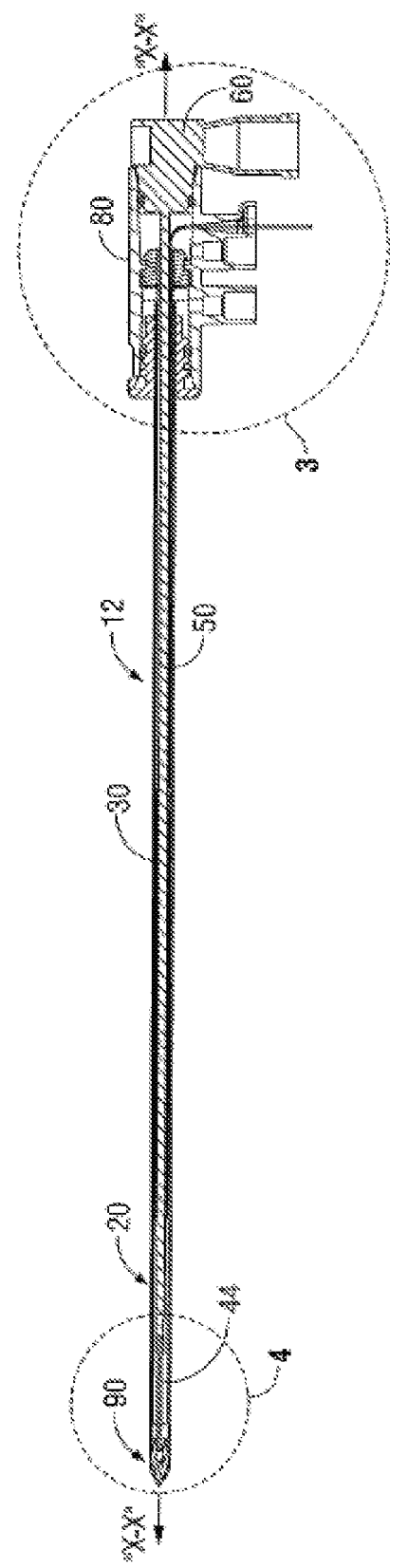
FIG. 2 is a longitudinal, cross-sectional view of a microwave antenna probe of the microwave ablation system of FIG. 1.

It has been found that non-directional ablation antennas can be made directional by placing metalized reflectors directly onto the radiating section of the antenna, e.g., using adhesives. The metalized reflector acts as an electromagnetic shield and blocks the radiation of energy through the section of the antenna upon which the reflector is disposed. Thus, a desired directionality can be achieved by selectively covering section(s) of the antenna with reflector(s) such that energy will radiate only in the direction(s) of the section(s) of the antenna that are left uncovered.

Turning now to FIGS. 1-7, a microwave ablation system is shown generally identified by reference numeral 10. It should be appreciated the present disclosure may be used with any suitable microwave ablation system and is not to be limited to the system disclosed herein, which is shown for illustrative purposes. Microwave ablation system 10 includes a microwave antenna probe 12 configured to couple to a microwave generator (not shown) via a flexible coaxial cable 16. Although the present disclosure is shown and described with reference to microwave antenna probes, the present disclosure is equally applicable for use in any suitable energy-based surgical instrument.

With continued reference to FIGS. 1-7, microwave antenna probe 12 generally includes an antenna assembly 20, an outer jacket and trocar assembly 70, and a connection hub 80. Antenna assembly 20 defines a longitudinal axis "X-X" and includes a radiating section that defines a dipole configuration, e.g., the radiating section includes a feed gap 43 and proximal and distal radiating portions 42, 44. A feedline 30 extends proximally from the radiating section into connection hub 80, ultimately coupling to cable 16 via transition 60 to connect antenna assembly 20 to the generator (not shown) for supplying energy thereto. Feedline 30 defines a coaxial configuration having an inner conductor 32 surrounded by an insulator 34. Insulator 34, in turn, is surrounded by an outer conductor 36, thus defining the coaxial configuration of feedline 30. Feedline 30 may be formed from a semi-rigid or flexible coaxial cable, although other configurations are also contemplated.

Figure 7:
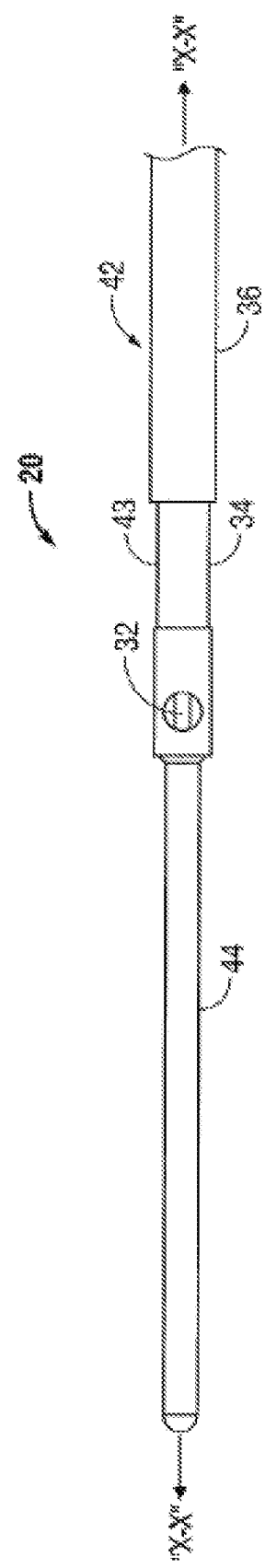
FIG. 7 is an enlarged view of the area of detail indicated as "7" in FIG. 6.

As mentioned above, and with reference to FIGS. 2, 4, and 6-7, the radiating section of antenna assembly 20 includes feed gap 43, proximal radiating portion 42, and distal radiating portion 44. Feed gap 43 is defined by the portion of inner conductor 32 and insulator 34 of feedline 30 that extends distally from outer conductor 36, e.g., outer conductor 36 may be stripped from the distal end of coaxial feedline 30 to define feed gap 43. Proximal radiating portion 42 is defined by the portion of feedline 30 disposed between the proximal end of feed gap 43 and the distal end of the choke 50. Distal radiating portion 44 is attached to feed gap 43 via any suitable process and extends distally therefrom. For example, as shown in FIG. 7, distal radiating portion 44 may be soldered to inner conductor 32 of feed gap 43 to establish electromechanical contact therebetween.

Antenna assembly 20, as shown in FIGS. 2, 4, and 6-7, further includes a choke or balun 50 disposed about feedline 30. Choke 50 includes an inner dielectric layer and an outer conductive layer. Choke 50 may be a quarter-wavelength shorted choke that is shorted to outer conductor 36 of feedline 30 at the proximal end of choke 50, although other configurations are contemplated. The dielectric layer of choke 50 may also be configured to extend distally beyond the conductor layer thereof towards the distal end of antenna assembly 20. Choke 50 is used to prevent the back travel of radiation through antenna assembly 20, and confines the radiation to the radiation portions 42, 44 of antenna assembly 20.

Figure 3:
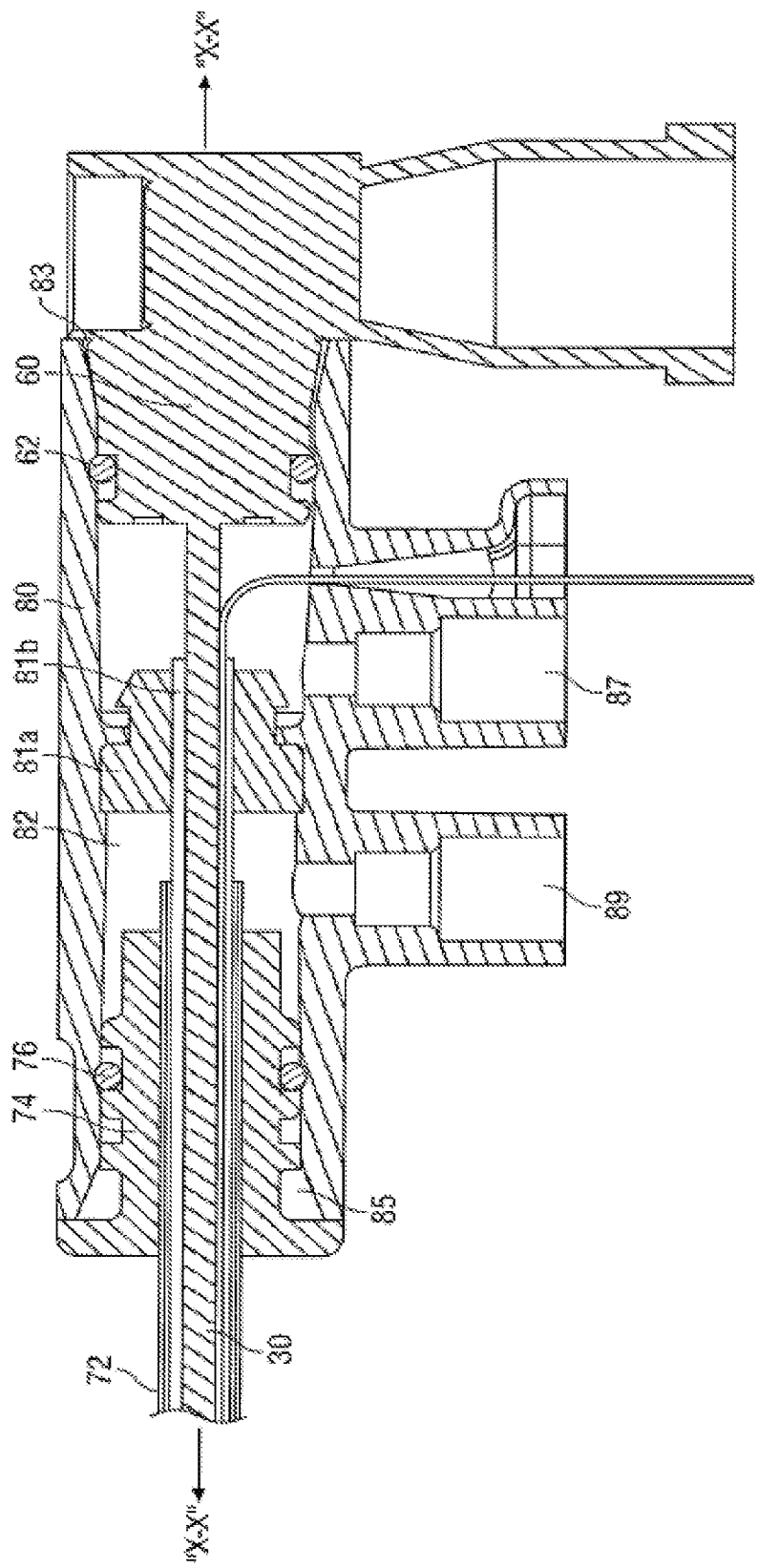
FIG. 3 is an enlarged view of the area of detail indicated as "3" in FIG. 2.

With additional reference to FIG. 3, as mentioned above, antenna assembly 20 includes a transition 60 from which feedline 30 extends. Feedline 30 extends into transition 60, wherein inner conductor 32 is coupled to an inner conductor (not explicitly shown) of coaxial cable 16 and outer conductor 36 is coupled to an outer conductor (not explicitly shown) of coaxial cable 16, while maintaining the spacing therebetween via an insulator (not explicitly shown). Cable 16 may be secured to feedline 30 within transition 60 via soldering, laser welding, or any other suitable process for establishing electromechanical contact therebetween. Transition 60 is disposed within proximal port 83 of connection hub 80 and is sealingly engaged therein via O-ring 62. More specifically, during assembly, the radiating section and feedline 30 of antenna assembly 20 are inserted through proximal port 83 and lumen 82 of connection hub 80 such that transition 60 may ultimately be inserted into proximal port 83 of connection hub 80 to sealingly engage transition 60 within proximal port 83 of connection hub 80 via O-ring 62. Antenna assembly 20 may be engaged within connection hub 80 during manufacturing, or may be assembled by the user.

Outer jacket and trocar assembly 70, as best shown in FIGS. 1-5, includes an outer jacket 72 configured to surround antenna assembly 20, e.g., proximal and distal radiating portions 42, 44, feed gap 43, and feedline 30, such that a coolant fluid may be circulated thereabout to maintain antenna assembly 20 in a relatively cooled state during use, although in some embodiments, cooling is not provided. A ferrule 74 is molded or otherwise engaged about outer jacket 72 towards the proximal end thereof to facilitate sealing engagement of the proximal end of outer jacket 72 within distal port 85 of connection hub 80 via O-ring 76. That is, during assembly, ferrule 74 and, thus, the proximal end of outer jacket 72, are inserted proximally into distal port 85 of connection hub 80 sufficiently such that ferrule 74 is sealingly engaged within connection hub 80 via O-ring 76. Similarly as above, outer jacket and trocar assembly 70 may be engaged within connection hub 80 during manufacturing, or may be assembled by the user.

Outer jacket and trocar assembly 70 further includes a trocar 90 defining a tapered distal end that terminates at a pointed distal tip 92 to facilitate insertion of microwave antenna probe 12 into tissue with minimal resistance, although other configurations may also be provided. Trocar 90 may be formed from a variety of heat-resistant materials suitable for penetrating tissue, e.g., metals (stainless steel, for example), various thermoplastic materials (such as polyetherimide, polyamide thermoplastic resins, etc.), or any other suitable material. Base 94 of trocar 90 is sealingly engaged within open distal end 78 of outer jacket 72 via any suitable process, e.g., using adhesives or via soldering. As such, trocar 90 sealingly encloses antenna assembly 20 within outer jacket 72 and connection hub 80.

Referring still to FIGS. 1-5, connection hub 80, as mentioned above, defines a longitudinal lumen 82 that is configured to receive feedline 30 therethrough, while sealingly engaging outer jacket 72 within distal port 85 and transition 60 within proximal port 83. Connection hub 80 further includes an inlet fluid port 87 and an outlet fluid port 89 that are disposed in fluid communication with lumen 82. Inlet and outlet ports 87, 89 are configured to receive tubes 17, 19 (see FIG. 1), respectively, such that coolant fluid from a coolant fluid supply (not shown) may be circulated through connection hub 80 and outer jacket 72. More specifically, a hub divider 81a is sealingly engaged within lumen 82 of connection hub 80 to isolate the inlet and outlet portions of lumen 82 of connection hub 80 from one another. Further, an inflow tube 81b is coupled to hub divider 81a and extends distally through outer jacket 72. As such, coolant fluid may flow from the coolant fluid source, through tube 17 and inlet port 87, into the inlet portion of lumen 82, and distally through inflow tube 81b, ultimately returning proximally through outer jacket 72 (exteriorly of inflow tube 81b), the outlet portion of lumen 82, outlet port 89, tube 19, and, ultimately, to the coolant fluid source. This configuration allows for the circulation of coolant fluid about antenna assembly 20 to maintain antenna assembly 20 in a relatively cooled state during use. The coolant fluid may be a liquid, gas, other flowable material, or combination thereof.

In operation, microwave energy having a wavelength, lambda ($\lambda$), is transmitted through antenna assembly 20, e.g., along the proximal and distal radiating portions 42, 44 and radiated into the surrounding medium, e.g., tissue. Radiation is emitted from antenna assembly 20 in all radial directions. The length of the antenna for efficient radiation may be dependent on the effective wavelength $\lambda_{eff}$, which is dependent upon the dielectric properties of the medium being radiated. Antenna assembly 20 through which microwave energy is transmitted at wavelength $\lambda$ may have differing effective wavelengths $\lambda_{eff}$ depending upon the surrounding medium, e.g., liver tissue, as opposed to breast tissue. Frequencies used in microwave ablation systems are in the low-frequency spectrum, such as between 915 MHz and 2.4 GHz, while the frequencies used in RF ablation systems are typically much lower, usually between 450 and 500 kHz.

As noted above, radiation from antenna assembly 20 is emitted in all radial directions. In order to focus the radiation from antenna assembly 20, one or more reflector strips is applied to antenna probe 12 to inhibit radiation in certain direction(s). Exemplary reflector strips provided in accordance with the present disclosure are detailed below with respect to FIGS. 8-14.

Figure 8:
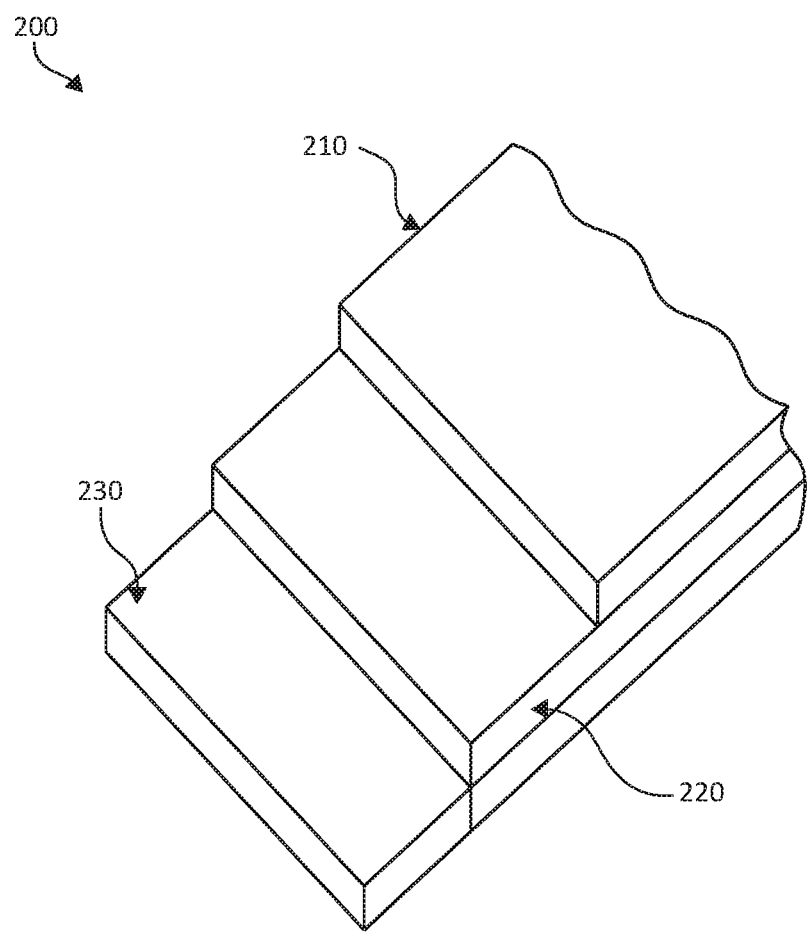
FIG. 8 is a perspective view of a portion of a reflector strip for a microwave antenna probe provided in accordance with the present disclosure.

Referring now to FIG. 8, a portion of a reflector strip in accordance with the present disclosure is shown, identified by reference numeral 200. Reflector strip 200 includes a shield 210 and an adhesive 220 disposed on one of the surfaces of shield 210. Shield 210 is formed of a metallic reflector configured to inhibit radiation of energy, e.g., microwave radiation, therethrough. Adhesive 220 enables the adherence of reflector strip 200 to another surface, e.g., the outer surface of antenna probe 12 (FIG. 1). In embodiments, reflector strip 200 further includes a release liner 230 disposed over adhesive 220. Release liner 230 is configured to be removed from reflector strip 200 before use to expose adhesive 220. Release liner 230 may be used to prevent adhesive 220 from losing its adhesive properties and/or prematurely adhering to a surface during manufacture, packaging, storage, use, etc. Release liner 230 may be composed of, for example, Super Calendared Kraft Paper, Clay Coated Kraft Paper, PET film, or Polyolefins. Release liner 230 may be coated with a release agent 231, such as silicone, polyvinyl alcohol, or any other release agent with a low surface energy to facilitate removal from adhesive 220. In embodiments, a common release liner 230 may include a plurality of reflector strips 200 disposed thereon. In such embodiments, when use of one of the reflector strips 200 is desired, the shield 210 together with the adhesive 220 is removed from the release liner 230 to expose the adhesive 220.

Once release liner 230 is peeled away or removed, in embodiments where so provided, reflector strip 200 may be placed onto proximal and distal radiating portions 42, 44 of antenna probe 12 (FIG. 1) and adhered thereto using adhesive 220. In embodiments, adhesive 220 is pressure sensitive. Adhesive 220 may be bonded to antenna probe 12 (FIG. 1) by hand through an application of pressure, such as by pushing the top surface of reflector strip 200 downward onto antenna probe 12 (FIG. 1) so that a fluid-tight seal is made between adhesive 220 and antenna probe 12 (FIG. 1). In embodiments, an application tool (not shown) may be used to facilitate application of reflector strip 200 onto antenna probe 12 (FIG. 1) and establishment of a fluid-tight seal therebetween.

Adhesive 220 may be any suitable adhesive for adhering metallic reflector shield 210 to the outer surface of antenna probe 12 (FIG. 1). For example, adhesive 220 may be formed from acrylic, cyanoacrylate, epoxy, urethane, butyl, foamed cored acrylic mass, rubber, or silicon. In embodiments, adhesive 220 will have a relatively high peel strength and adhesion to the surface of antenna probe 12 (FIG. 1), such that reflector strip 200 remains in place during insertion through tissue, contact with fluids, and during tissue ablation. In embodiments, adhesive 220 may be non-permanent, such that reflector strip 200 may be removed from the surface of antenna probe 12 after tissue ablation is completed, or if directionality is no longer desired or necessary. In embodiments, adhesive 220 is insoluble, resistant to water, chemicals, and radiation. In embodiments, adhesive 220 may be formed of a biocompatible material meeting the ISO 10993 standard.

In embodiments, adhesive 220 may be thermosetting. For example, adhesive 220 may be activated to bond reflector strip 200 to antenna probe 12 (FIG. 1) when antenna probe 12 (FIG. 1) is powered on and emitting radiation, via the process of cross-linking. In embodiments, an external heat source may be used to set the thermosetting adhesive 220 to bond reflector strip 200 to antenna probe 12.

Figure 9:
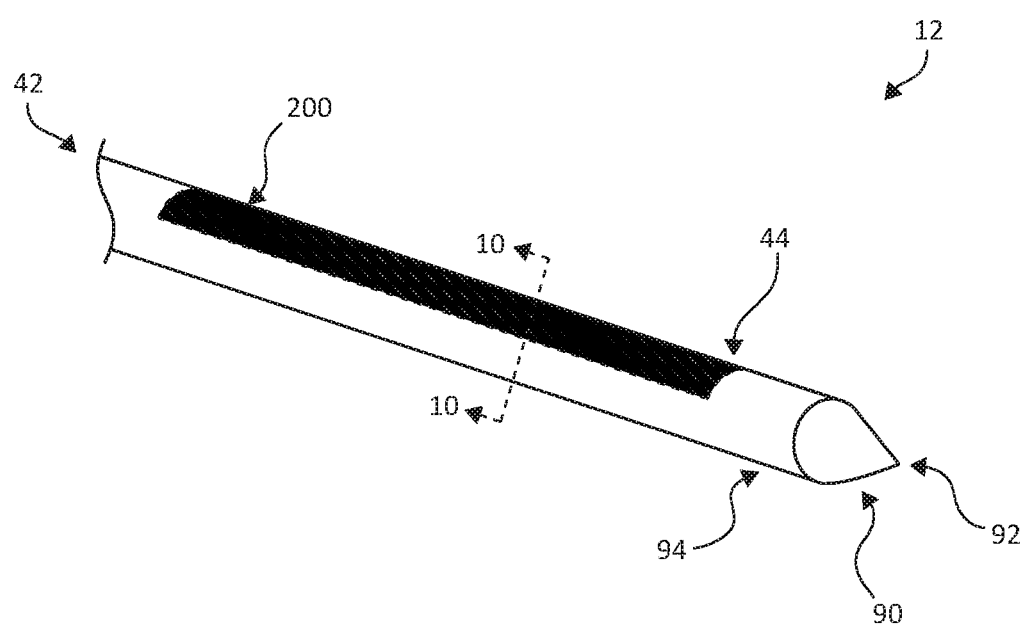
FIG. 9 is a perspective view of a reflector strip adhered to an antenna probe.
Figure 10:
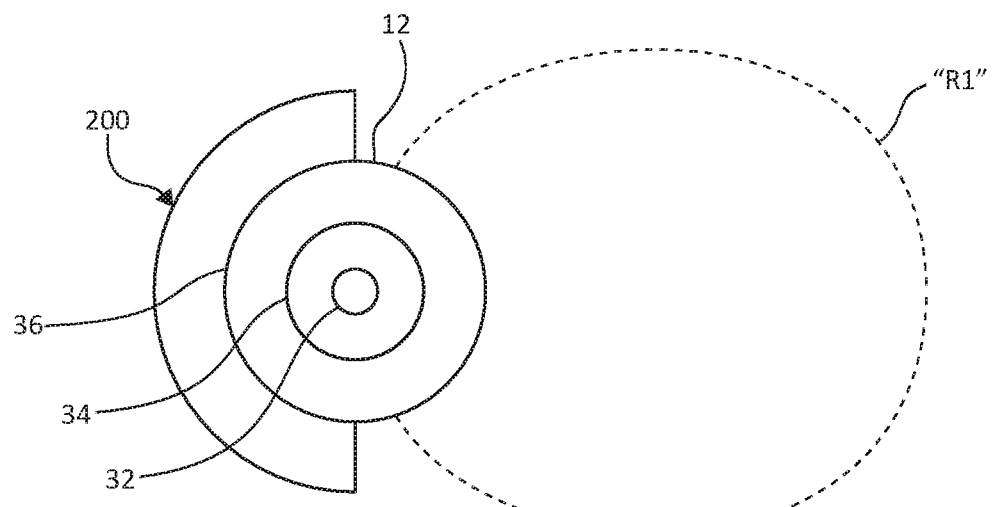
FIG. 10 is a transverse, cross-sectional view taken across section line "10-10" of FIG. 9, illustrating a radiation pattern emitted from the antenna probe.

Referring now to FIGS. 9 and 10, reflector strip 200 is shown adhered to antenna probe 12. Reflector strip 200 extends the entire length from proximal radiating portion 42 to distal radiation portion 44 and covers approximately ½ the circumference of antenna probe 12. As a result of this configuration, as shown in FIG. 10, radiation pattern "R1" is emitted when antenna probe 12 is powered on. More specifically, radiation is only emitted from the portions of antenna probe 12 that are not covered by reflector strip 200.

Figure 11:
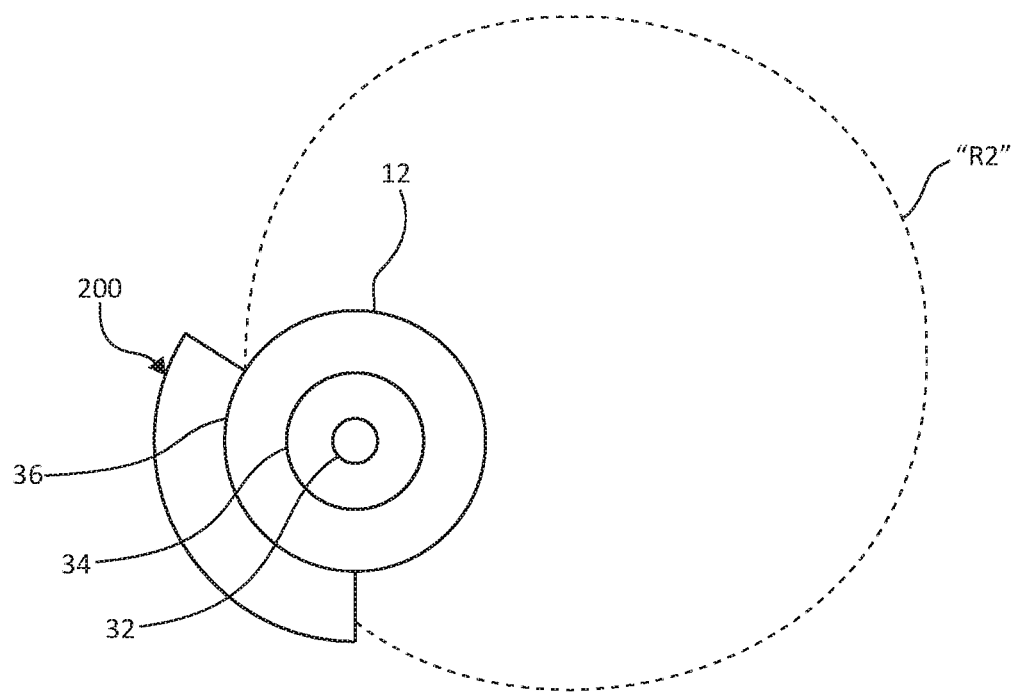
FIG. 11 is a transverse, cross-sectional view of another reflector strip adhered to the antenna probe of FIG. 10, illustrating a radiation pattern emitted therefrom.
Figure 12:
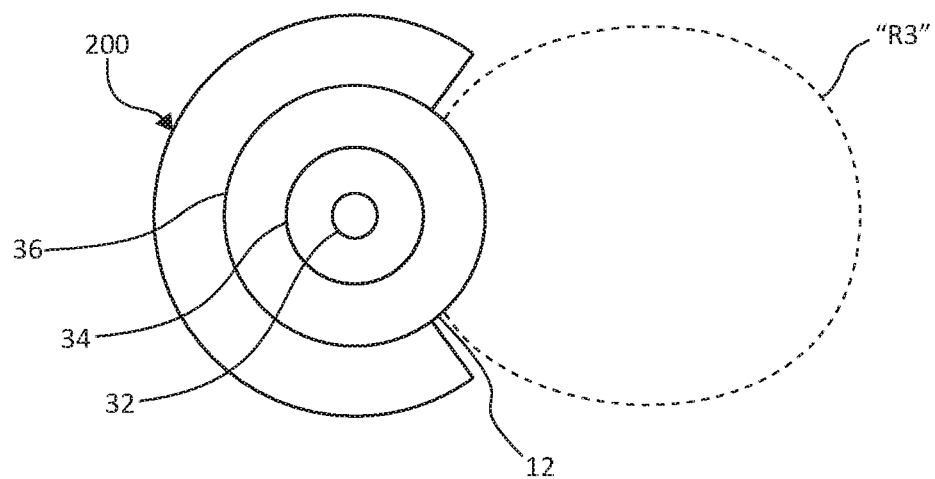
FIG. 12 is a transverse, cross-sectional view of yet another reflector strip adhered to the antenna probe of FIG. 10, illustrating a radiation pattern emitted therefrom.
Figure 13:
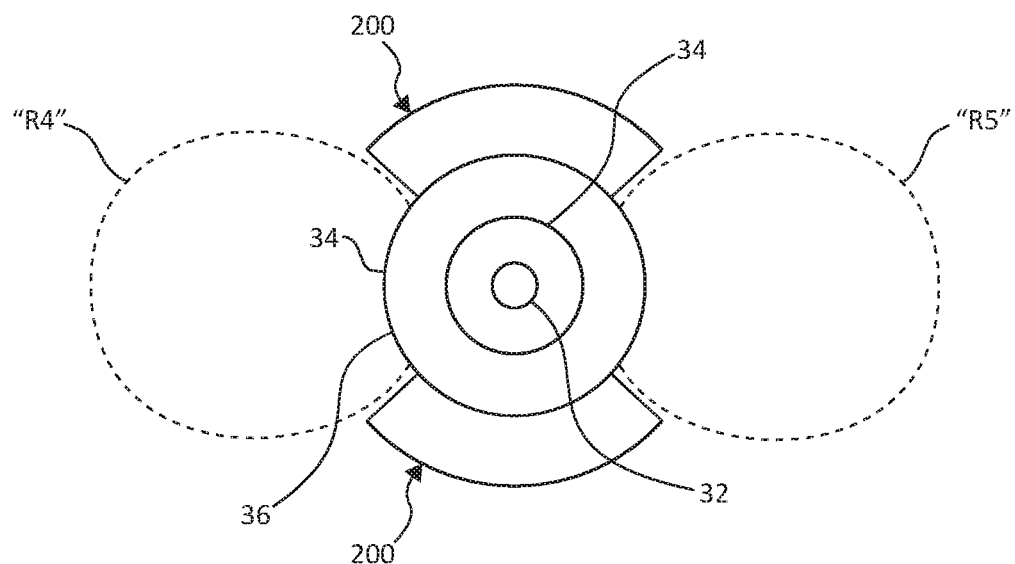
FIG. 13 is a transverse, cross-sectional view of still another reflector strip adhered to the antenna probe of FIG. 10, illustrating a radiation pattern emitted therefrom.

It should be appreciated that reflector strip 200 may define any suitable configuration and may be placed at any location, or at any plurality of locations, on proximal and distal radiating portions 42, 44 of antenna probe 12. For example, FIG. 11 depicts a reflector strip 200 covering ¼ the circumference of the antenna probe 12, while FIG. 12 depicts a reflector strip 200 covering ¾ the circumference of antenna probe 12. Thus, radiation pattern "R2" is larger than radiation pattern "R1," while radiation pattern "R3" is smaller than that of radiation pattern "R1." FIG. 13 depicts reflector strips 200 placed at two locations, such that two radiation patterns "R4" and "R5" are emitted from antenna probe 12. In embodiments, one or more reflector strips 200 may be placed on antenna probe 12 to define a desired radiation pattern having any shape, size, and/or configuration.

In embodiments, reflector strip 200 may be manufactured in the form of a sheet so that it can be cut into any desired configuration for a specific application. Markings on the sheet may be provided to enable a user to readily identify where to cut to produce a desired reflector strip 200. For example, markings may be provided to indicate where cuts should be made to produce a reflector strip 200 to cover ¼, ½, or ¾ of the circumference of antenna probe 12.

In embodiments, reflector strip 200 may be placed on a roll, similar to those used in label dispensers or label applicators. In embodiments, plural reflector strips 200 on the roll may be pre-cut into different configurations such that a user may remove the appropriate reflector strip 200 corresponding to the radiation pattern desired.

Figure 14:
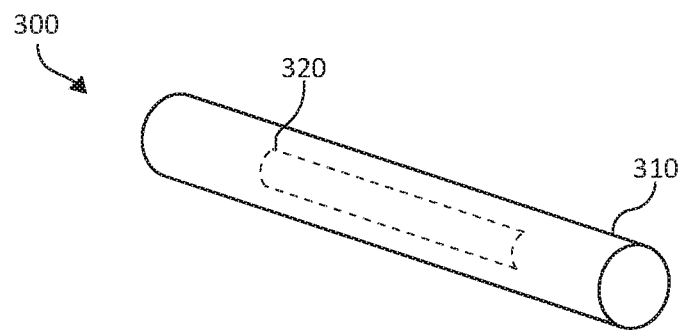
FIG. 14 is a perspective view of a reflector tube for a microwave antenna probe provided in accordance with the present disclosure.

In embodiments, rather than providing reflector strips 200 that are configured to be adhered to antenna probe 12 to achieve a desired radiation pattern, a reflector strip 200 configured to fully cover radiating portions 42, 44 of antenna probe 12 may be provided. In such embodiments, reflector strip 200 may have perforations and/or markings to allow a user to remove the portion(s) of reflector strip 200 where radiation emission is desired, similarly as detailed below with respect to reflector tube 300 (FIG. 14).

In embodiments, various different reflector strips 200 according to some or all of the above-embodiments may be provided as a kit packaged in a disposable sterile surgical pack to enable a user to configure antenna probe 12 to a desired configuration using one or more of the reflector strips 200.

Regardless of the particular configuration of reflector strip(s) 200 used, shield 210 of reflector strip 200 provides directionality by providing electromagnetic interference ("EMI") shielding to the radiating portions of antenna probe 12 it is covering. EMI reduces or eliminates the electromagnetic field in a space by blocking the field with barriers made of conductive materials. In embodiments, shield 210 may be made of any suitable material, such as silver, copper, gold, aluminum, brass, bronze, tin, lead, nickel, stainless steel, electrically conductive polymers, mumetal, superpermalloy, combinations thereof, or the like. Such materials may also aid in radiographic or ultrasound location of the reflector strip 200 during ablation procedures. In embodiments, shield 210 may be a composite material or materials to enhance EMI shielding, such as, for example, having a layer of gold and a separate layer of copper. In yet other embodiments, shield 210 may be a strip of material, foil, thin sheet, tape, mesh, coating, or the like.

The thickness of shield 210 may be varied depending on the specific surgical application or the level of Shielding Effectiveness ("SE") required. SE is the ratio of the electromagnetic (or RF) energy before shielding and its intensity after shielding. This value is used for measuring the effectiveness of EMI shielding. SE is expressed in decibels (dB) and represents the sum of all losses in the shielding. The formula used for calculation of SE may be expressed as $dB = 20 \log_{10}(F1/F2)$, where F1 is the field measurement before shielding and F2 is the field measurement after shielding. The above formula shows dB ranges falling along a logarithmic scale. For example, a rating of 50 dB indicates a shielding strength ten times that of 40 db.

In general, a SE of 10 to 30 dB provides the lowest effective level of shielding, while anything below that range can be considered little or no shielding. A SE of 40 dB is usually the targeted minimum. SE between 60 and 90 dB is considered a high level of protection, while 90 to 120 dB is exceptional. Generally, for microwave ablation where the operating frequencies are between 915 MHz and 2.4 GHz, a SE of 40 dB to 50 dB will provide at least 99.9% attenuation (protection or blockage) against electromagnetic radiation.

In embodiments, shield 210 may be coated with Teflon™, or any other suitable non-stick coating to reduce friction during insertion into the body cavity and/or tissue. In embodiments, shield 210 may be preprinted, embossed, or the like, with units of measurement or other locational elements for precision placement onto antenna probe 12 and/or to enable accurate placement of antenna probe 12 within target tissue. In embodiments, the edges of shield 210 may be beveled, rounded, or the like, to prevent reflector strip 200 from catching onto adjacent tissue and other bodily surfaces.

In accordance with the present disclosure, and with reference to FIG. 14, another embodiment of a reflector, in the form of a tube, is shown and generally designated as 300. Reflector tube 300 may include a metallic reflector shield 310 and one or more windows 320. Reflector tube 300 is configured such that it is capable of being slipped over and fitted to the radiating portion of antenna probe 12. Reflector tube 300 may define any suitable size or shape for placement onto any type of antenna. The one or more windows 320 may likewise define any suitable size or shape to achieve a desired radiation pattern when used in conjunction with an antenna.

Once in place, antenna probe 12 only emits radiation from window 330, while radiation from any other area covered by reflector tube 300 is blocked (i.e., is shielded). Reflector tube 300 may be manufactured with or without windows 320. For example, if reflector tube 300 is manufactured without windows, a user may use a skiving tool to form windows 320 at a desired location(s) on reflector tube 300. Perforations and/or markings on reflector tube 300 may be provided to facilitate formation of windows 320 of a desired configuration. In embodiments, reflector tube 300 may be open at one end, such that it can be slipped over antenna probe 12, and closed at the other end, such that the tip of the antenna is encased therein. In such embodiments, the closed end of reflector tube 300 may have a geometry sufficient to properly encase the tip of the particular antenna used therewith. Alternatively, both ends of reflector tube 300 may be open, as illustrated in FIG. 14.

Figure 15:
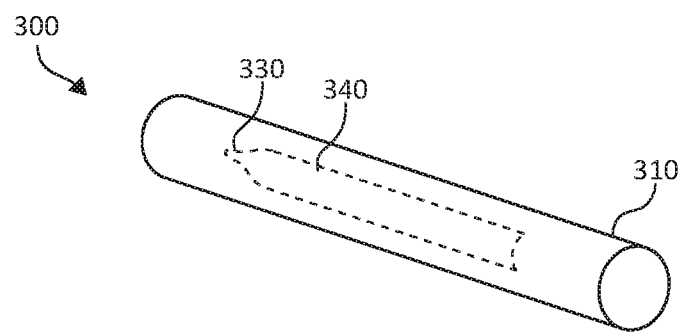
FIG. 15 is a perspective view of another reflector tube for a microwave antenna probe provided in accordance with the present disclosure.
Figure 16:
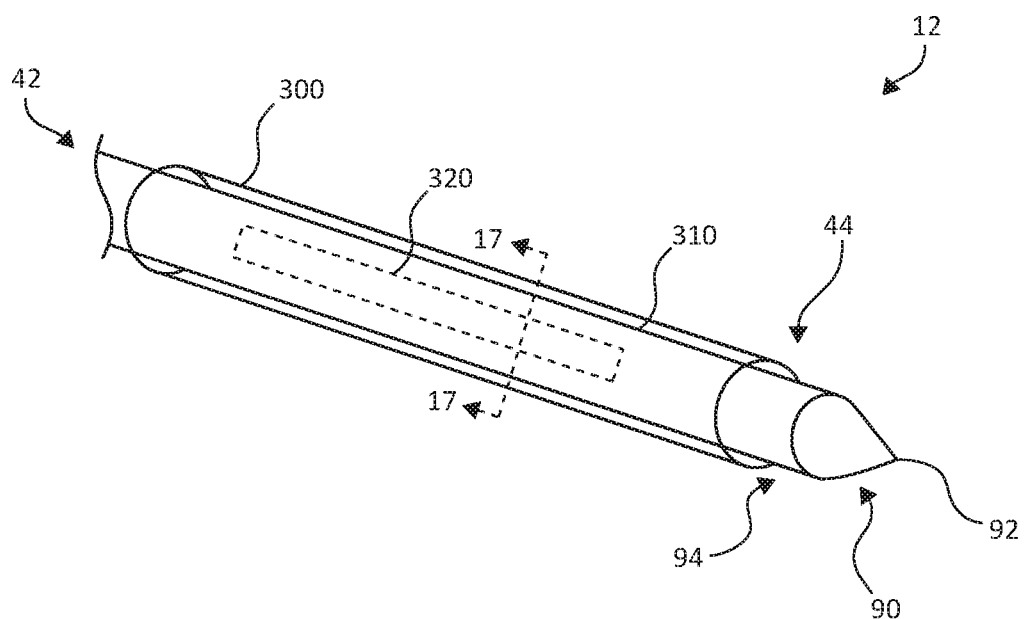
FIG. 16 is a perspective view of a reflector tube adhered to an antenna probe.
Figure 17:
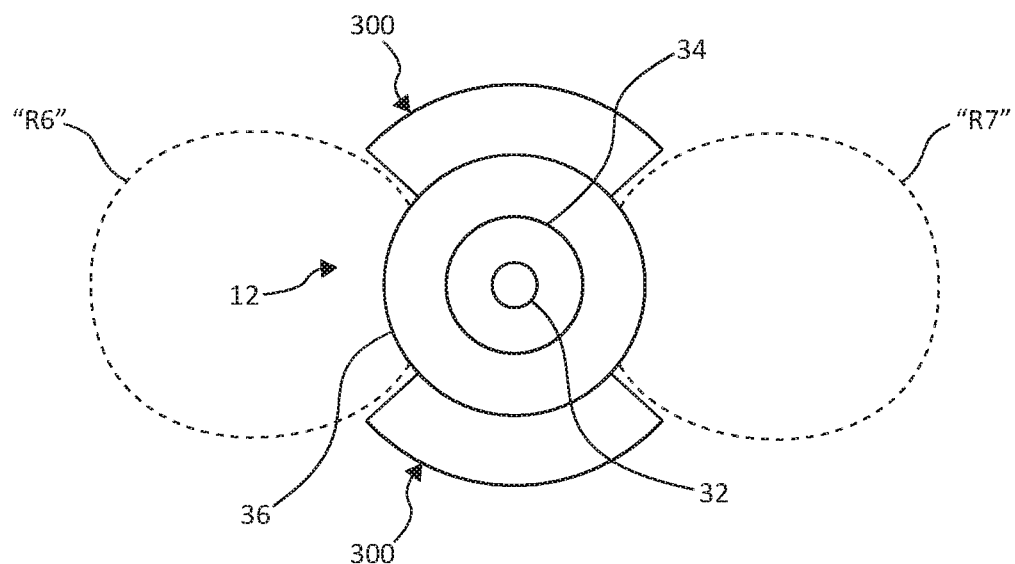
FIG. 17 is a transverse, cross-sectional view taken across section line "17-17" of FIG. 16, illustrating a radiation pattern emitted from the antenna probe.

Referring also to FIG. 15, reflector tube 300 may have one or more window screens 340 covering one or more of the windows 320 thereof, and a pull tab 330 associated with each window screen 340. A user may thus pull on pull tab 330 to facilitate remove of the associated window screen 340 to reveal the corresponding window 320. In embodiments, the window screens 340 may be repositioned within the corresponding window 320 when exposure of that particular window 320 is no longer wanted. The above-detailed configuration of screens 340 and windows 320 may be advantageous, for example, if a user desires to have a plurality of windows 320 emitting radiation therefrom. For example, a surgeon may ablate a cancerous tumor in a patient, which requires only a single window 320. The same patient may have additional tumors, such as, for example, two adjacent tumors opposing each other, which require opposing radiation fields. The surgeon may then simply remove a second window screen 340 from reflector tube 300 to reveal a second window 320 and ablate both tumors at once, all in a single procedure without the need for retooling. FIGS. 16 and 17 depict a reflector tube 300 adhered to the surface of an antenna probe 12 with two windows 320 such that two opposing radiation fields "R6" and "R7" are emitted from antenna probe 12 during use.

In embodiments, the surgeon may use reflector tube 300 for only part of a surgical procedure where precision tissue targeting is required. The reflector tube 300 may then be removed and antenna probe 12 used there without for the remainder of the procedure (or until reflector tube 300 or another reflector tube is once again required) to target other areas of tissue, where such precision is not necessary. Reflector tube 300 may be rolled, peeled, tore, or cut off antenna probe 12 after use. In embodiments, reflector tube 300 may have for example, perforations, or the like, along its surface to aid in its removal from antenna probe 12.

In embodiments, reflector tube 300 may be a shrinkable tube, such as, for example, a heat shrink. After slipping reflector tube 300 over antenna probe 12, reflector tube 300 may be heat-shrunk onto antenna probe 12 by powering on microwave ablation system 10, which provides sufficient heat to shrink reflector tube 300 and provide a tight seal over antenna probe 12. An external heat source may also be used to fit reflector tube 300 to antenna probe 12 via heatshrinking. Additionally or alternatively, a thermoplastic adhesive on the inner surface of reflector tube 300 may be used to establish a fluid-tight seal between reflector tube 300 and antenna probe 12. In embodiments, reflector tube 300 may alternatively be vacuum sealed onto antenna probe 12.

Figure 4:
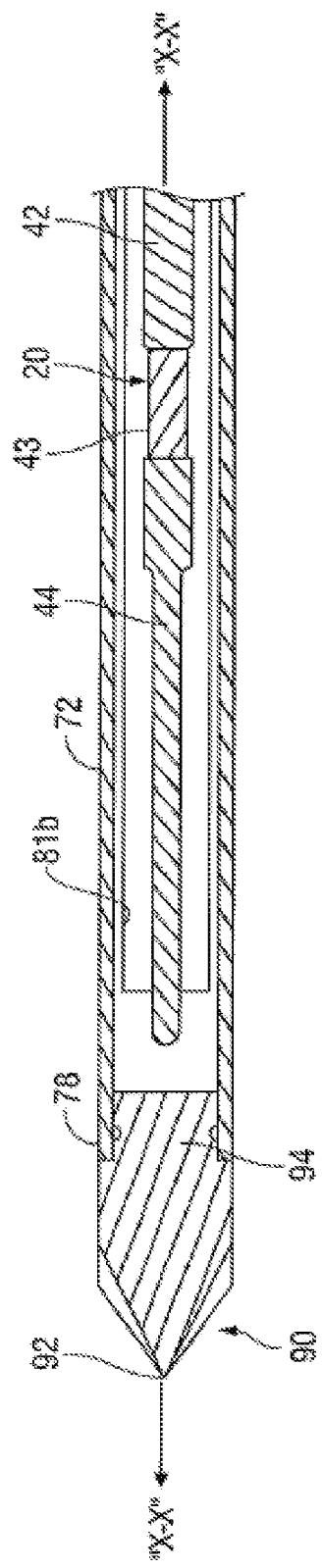
FIG. 4 is an enlarged view of the area of detail indicated as "4" in FIG. 2.
Figure 5:
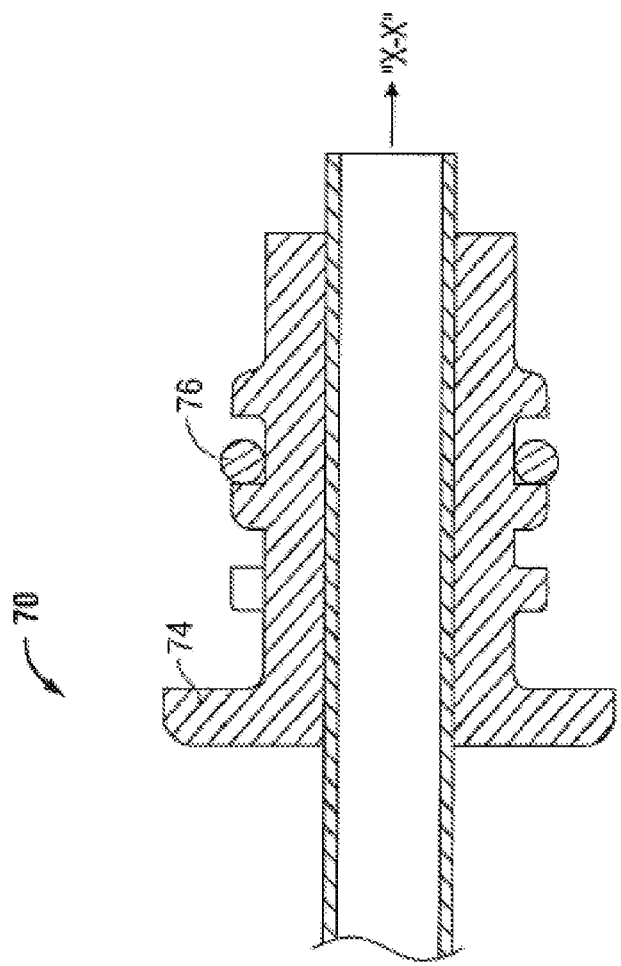
FIG. 5 is a longitudinal, cross-sectional view of an outer jacket and trocar assembly of the microwave antenna probe of FIG. 2.
Figure 5:
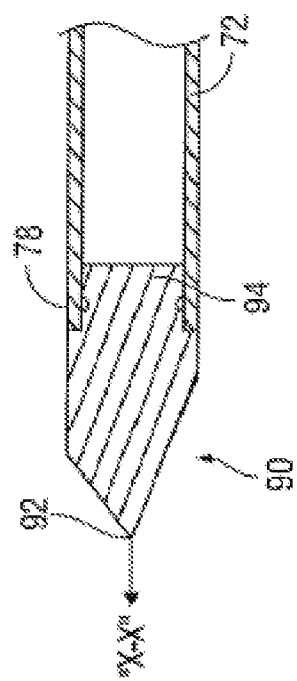
Figure 6:
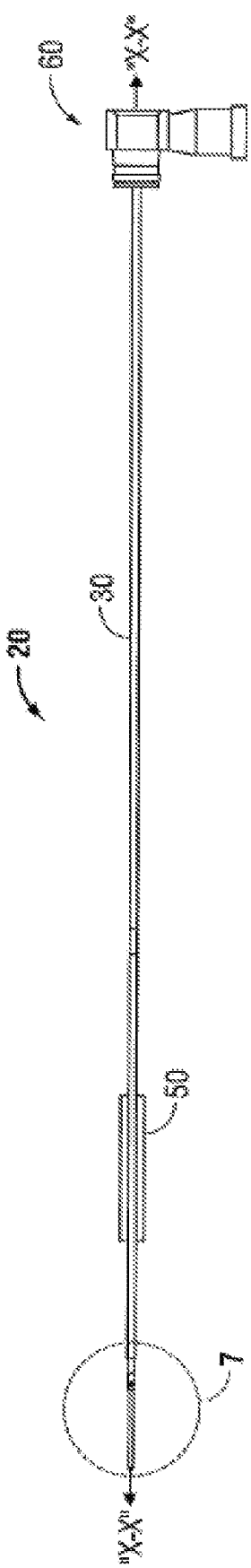
FIG. 6 is a side view of an antenna assembly of the microwave antenna probe of FIG. 2.
Figure 18:
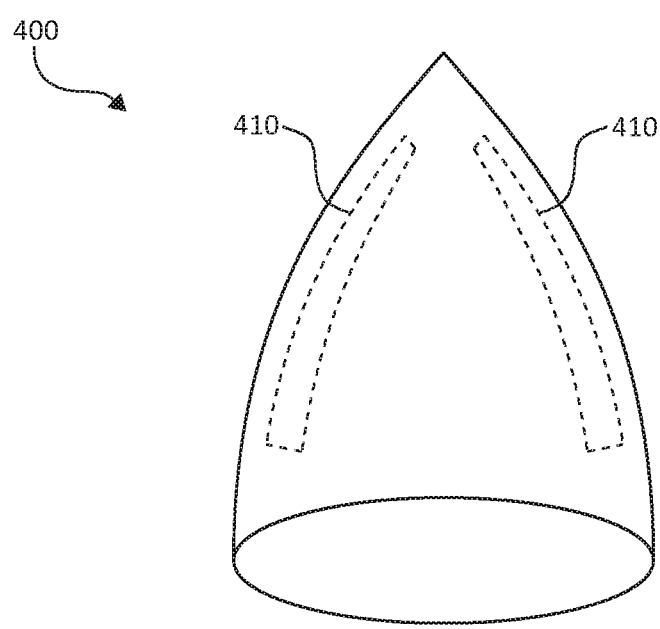
FIG. 18 is a perspective view of a reflector cap for a microwave antenna probe provided in accordance with the present disclosure.

Referring now to FIG. 18 in conjunction with FIG. 4, a cap is shown and generally designated as 400. Cap 400 is placed over trocar 90 and distal tip 92 of antenna probe 12. Cap 400 may be used alone or in combination with reflector strip 200 and/or reflector tube 300 to prevent unwanted emission of radiation from the distal tip 92 of antenna probe 12. In embodiments, cap 400 may be formed of any material and having the same or similar properties described in the embodiments of the reflectors 200 or 300 above. Usually, the distal tips of antennas have a triangular, cone-shaped, or semi-circular geometry, such that a strip of material may be difficult to adhere without folds or kinks or may otherwise be unable to provide sufficient coverage. Accordingly, cap 400 is configured to fit over the tip geometry of an antenna and provide sufficient shielding. In embodiments, cap 400 may also have windows or slots 410, pre-formed or formed via user-removal of material, such that directionality can be achieved in the tip of the antenna itself, thus achieving further directional precision for tissue ablation. In embodiments, cap 400 may be placed in a surgical kit with reflector strip 200 and/or reflector tube 300.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended thereto.

What is claimed is:

1. An ablation system for directing energy to a target volume of tissue, comprising:
   a trocar assembly including an outer jacket and a trocar at a distal end of the outer jacket;
   an ablation antenna assembly positioned in the trocar assembly and including at least one radiating portion configured to output electromagnetic radiation; and at least one electromagnetic shielding reflector disposed on and configured to conform to an outer surface of the outer jacket of the trocar assembly, wherein the at least one electromagnetic shielding reflector is configured to block electromagnetic radiation from the at least one radiating portion such that a particular directionality of the electromagnetic radiation from the at least one radiating portion to a target volume of tissue is achieved and the at least one electromagnetic shielding reflector includes an electromagnetic shielding material, a distal-most end of the at least one electromagnetic shielding reflector disposed proximal to a distal-most end of the trocar.

2. The system of claim 1, wherein the at least one electromagnetic shielding reflector further includes a release liner releasably attached to an adhesive.

3. The system of claim 1, wherein the electromagnetic shielding material is selected from the group consisting of silver, copper, gold, aluminum, brass, bronze, tin, lead, nickel, stainless steel, electrically conductive polymer, mumetal, and superpermalloy.

4. The system of claim 1, wherein the electromagnetic shielding material is a composite material.

5. The system of claim 1, wherein the at least one electromagnetic shielding reflector has a configuration selected from the group consisting of a strip of material, a sheet, a foil, a mesh, a tape, and a coating.

6. The system of claim 1, wherein the at least one electromagnetic shielding reflector is configured as a tube and configured for fitted placement over at least a portion of the ablation antenna assembly.

7. The system of claim 6, wherein the tube is a heatshrink tube.

8. The system of claim 6, wherein an adhesive is disposed on an inner surface of the tube.

9. The system of claim 6, wherein the tube defines at least one window configured to permit passage of the electromagnetic radiation therethrough from the at least one radiating portion.

10. The system of claim 9, further comprising a removable screen configured to cover the at least one window to thereby inhibit the electromagnetic radiation therethrough from the at least one radiating portion.

11. The system of claim 1, wherein the at least one electromagnetic shielding reflector is configured for removable positioning on the outer surface of the outer jacket of the trocar assembly.

12. The system of claim 1, wherein the at least one electromagnetic shielding reflector is removably affixed to the outer surface of the outer jacket via an adhesive.

13. The system of claim 1, wherein the at least one electromagnetic shielding reflector is coaxial with the at least one radiating portion upon conforming to the outer surface of the outer jacket of the trocar assembly.

14. The system of claim 1, wherein the at least one electromagnetic shielding reflector and the outer jacket of the trocar assembly are concentric upon conforming of the at least one electromagnetic shielding reflector to the outer surface of the outer jacket of the trocar assembly.

15. A microwave antenna for delivering microwave energy to tissue, comprising: an inner conductor; an outer conductor defining a distal-most end; a dielectric material disposed between the inner and outer conductors; and a shielding reflector strip configured to inhibit radiation of microwave energy through the shielding reflector strip such that a particular directionality of the radiation of microwave energy to tissue is achieved, the shielding reflector strip conforming to an outer surface of the outer conductor for removable affixing of the conformed shielding reflector strip to the outer surface of the outer conductor via an adhesive, wherein a distal-most end of the shielding reflector strip is disposed proximal to the distal-most end of the outer conductor.

* * * * *